United States Patent
Lesk et al.

(10) Patent No.: US 7,971,998 B2
(45) Date of Patent: Jul. 5, 2011

(54) APPARATUS AND METHOD FOR MEASURING A DISPLACEMENT WITHIN AN EYE IN VIVO IN SITU, AND METHOD OF ASSESSMENT

(75) Inventors: Mark Lesk, Montreal (CA); Marcelo Wajszilber, Côte Saint-Luc (CA); Tsuneyuki Ozaki, Brossard (CA)

(73) Assignee: RSEM, Limited Partnership, Montreal, Quebec ( * ) Notice: Subject to any disclaimer, the term of this patent is extended or adjusted under 35 U.S.C. 154(b) by 0 days.

(21) Appl. No.: 12/515,100

(22) PCT Filed: Nov. 14, 2007

(86) PCT No.: PCT/CA2007/002043
§ 371 (c)(1),
(2), (4) Date: Jan. 11, 2010

(87) PCT Pub. No.: WO2008/058386

PCT Pub. Date: May 22, 2008

(65) Prior Publication Data
US 2010/0103377 A1    Apr. 29, 2010

Related U.S. Application Data

(60) Provisional application No. 60/866,086, filed on Nov. 16, 2006.

(51) Int. Cl.
*A61B 3/10*    (2006.01)
(52) U.S. Cl. ............................ 351/221; 351/200; 607/67
(58) Field of Classification Search .................. 351/200, 351/205, 221; 607/66–70
See application file for complete search history.

(56) References Cited

U.S. PATENT DOCUMENTS

| | | | |
|---|---|---|---|
| 5,148,807 A | 9/1992 | Hsu | |
| 5,396,303 A | 3/1995 | Peters et al. | |
| 5,828,454 A | 10/1998 | Gust | |
| 5,975,697 A | 11/1999 | Podoleanu et al. | |
| 6,325,512 B1 | 12/2001 | Wei | |
| 6,595,920 B2 | 7/2003 | Walton | |
| 7,404,640 B2 * | 7/2008 | Ferguson et al. | 351/221 |
| 2004/0061830 A1 | 4/2004 | Hellmuth et al. | |
| 2005/0030473 A1 | 2/2005 | Fahrenkrug et al. | |
| 2007/0171367 A1 | 7/2007 | Sebastian et al. | |

OTHER PUBLICATIONS

Bayerle-Eder et al., Effect of a nifedipine induced reduction in blood pressure on the association between ocular pulse amplitude and ocular fundus pulsation amplitude in systemic hypertension, www.bjophthalmol.com, Sep. 2007, pp. 704-708.

Friedenwald, Contribution to the theory and practice of tonometry, American Journal of Ophthalmology, vol. 20, Oct. 1937, pp. 985-1025.

Fercher, In Vivo Measurement of Fundus Pulsations By Laser Interferometry, IEEE Journal of Quantum Electronics, vol. QE-20, No. 12, Dec. 1984, pp. 1469-1471.

Weinbaum, A mathematical model for the elastic and fluid mechanical behavior of the human eye, Bulletin of Mathematical Biology, vol. 27, No. 2, 1965, pp. 1-3.

Silver et al., Pressure-volume relation for the living human eye, Current Eye Research, vol. 20, No. 2, 2000, pp. 115-120.

* cited by examiner

*Primary Examiner* — Huy K Mai
(74) *Attorney, Agent, or Firm* — Bereskin & Parr LLP

(57) ABSTRACT

The present invention relates to an apparatus and a method for measuring a displacement in vivo in situ of an eye, along with a method of assessing of an eye condition. More particularly, the apparatus and method of the present invention permits measurements of a displacement of at least two points in proximity of an optic disc, in the eye of a patient. For doing so, the apparatus uses a probing unit, an analog/digital converter and an analyzer. The displacement measured may include a pulsatile displacement of the lamina cribrosa, so as to perform early assessment of an eye condition.

16 Claims, 7 Drawing Sheets

APPARATUS AND METHOD FOR MEASURING A DISPLACEMENT WITHIN AN EYE IN VIVO IN SITU, AND METHOD OF ASSESSMENT

FIELD OF THE INVENTION

The present invention generally relates to the field of apparatuses and methods of assessment of eye diseases. More specifically, the invention relates to an apparatus and method for measuring displacement of a lamina cribrosa.

BACKGROUND OF THE INVENTION

Glaucoma is a group of eye diseases that share a distinct type of optic nerve damage that can lead to blindness. A major difficulty of this disease is that most people who have glaucoma do not notice any symptoms until they begin to lose substantial segments of their visual function and in particular visual field. This visual loss is permanent and irreversible. Another major difficulty is that, without years of monitoring individual patients, it is impossible for clinicians to distinguish patients with rapidly progressive glaucoma, the high-risk patients, from those with a more benign course. Consequently, there is no way to target high-risk patients for more aggressive therapy. Chronic glaucoma is truly "the silent blinding disease". The World Health Organization estimates that the number of people worldwide affected by glaucoma is approximately 13.5 million. Currently, about 300,000 Canadians are diagnosed with glaucoma and it is estimated that another 150,000 Canadians have glaucoma but remain undiagnosed.

Preventive detection of the most common type of glaucoma, primary open angle glaucoma, is challenging because until the disease is in an advanced stage, primary open-angle glaucoma is asymptomatic. Furthermore, because the lost field of vision is usually peripheral, i.e. outside of the region of central vision, patients do not notice it at first.

It is known that while a high intraocular pressure (IOP) is related to glaucoma. However, other factors such as disturbances of blood flow in the optic nerve head may interact with intraocular pressure to affect the optic nerve with or without elevated IOP. Furthermore, in many cases of primary open angle glaucoma, the patient's intraocular pressure is statistically normal which is referred to as normal tension glaucoma. In open angle glaucoma, early detection is further complicated by the fact that the intraocular pressure is commonly normal during standard clinical screening. Because optic nerve examination and perimeter testing are not always performed in addition to intraocular pressure measurement in normal screening visits of those patients at risk, normal tension glaucoma and open angle glaucoma are under diagnosed until the disease has resulted in irreversible damage to the vision.

Thus, identifying people with risk factors would permit the effective use of techniques that detect glaucoma in its early stages, and allow earlier treatment, which in some cases stabilize the progression of glaucoma.

There is currently no methodology to predict which patients' eyesight will deteriorate rapidly from those that will deteriorate slowly. Currently the only apparatus that can estimate the biomechanical properties of the eye in vivo in situ, a confocal scanning laser opthalmoscope, requires that the intraocular pressure be manipulated and that two imaging sessions occur several weeks or months apart. This process is neither rapid nor non-invasive. As of today, no rapid, non-invasive test to quantify the biomechanical properties of the eye in vivo in situ allowing clinicians to identify glaucoma patients at high risk of rapid visual field loss exist. Once identified, such high-risk patients could be treated more aggressively in order to prevent visual field loss.

SUMMARY OF THE INVENTION

It is an object of an aspect of the present invention to provide an apparatus for measuring displacement within an eye in vivo in situ. The apparatus comprises a probing unit, an analog/digital converter and an analyzer. The probing unit is adapted for probing in vivo in situ an eye for displacement of a point in or in proximity of an optic disc and generating a corresponding resulting probing signal. The analog/digital converter is adapted for converting the resulting probing signal into a digitalized resulting probing signal. The analyzer is adapted for analyzing the digitalized resulting probing signal and assessing therefrom displacement in proximity of the optic disc of the eye.

It is also another object of the present invention to provide a method for assessing condition of an eye in a patient. The method comprises measuring in vivo in situ displacement of a point in or in proximity of an optic disc of the eye and correlating the measured displacements with an eye condition.

In accordance with yet another aspect, the present invention provides a method for identifying an eye having an elevated risk of rapid visual field deterioration. The method comprises measuring in vivo in situ displacement of a point in or in proximity of an optic disc of the eye and correlating the measured displacement with an eye condition.

BRIEF DESCRIPTION OF DRAWINGS

These and other features of the present invention will become more apparent from the following description in which reference is made to the appended drawings wherein similar references denote similar parts.

DETAILED DESCRIPTION OF THE INVENTION

Optic Nerve Head Anatomy, Physiology and Pathology

Figure 1:
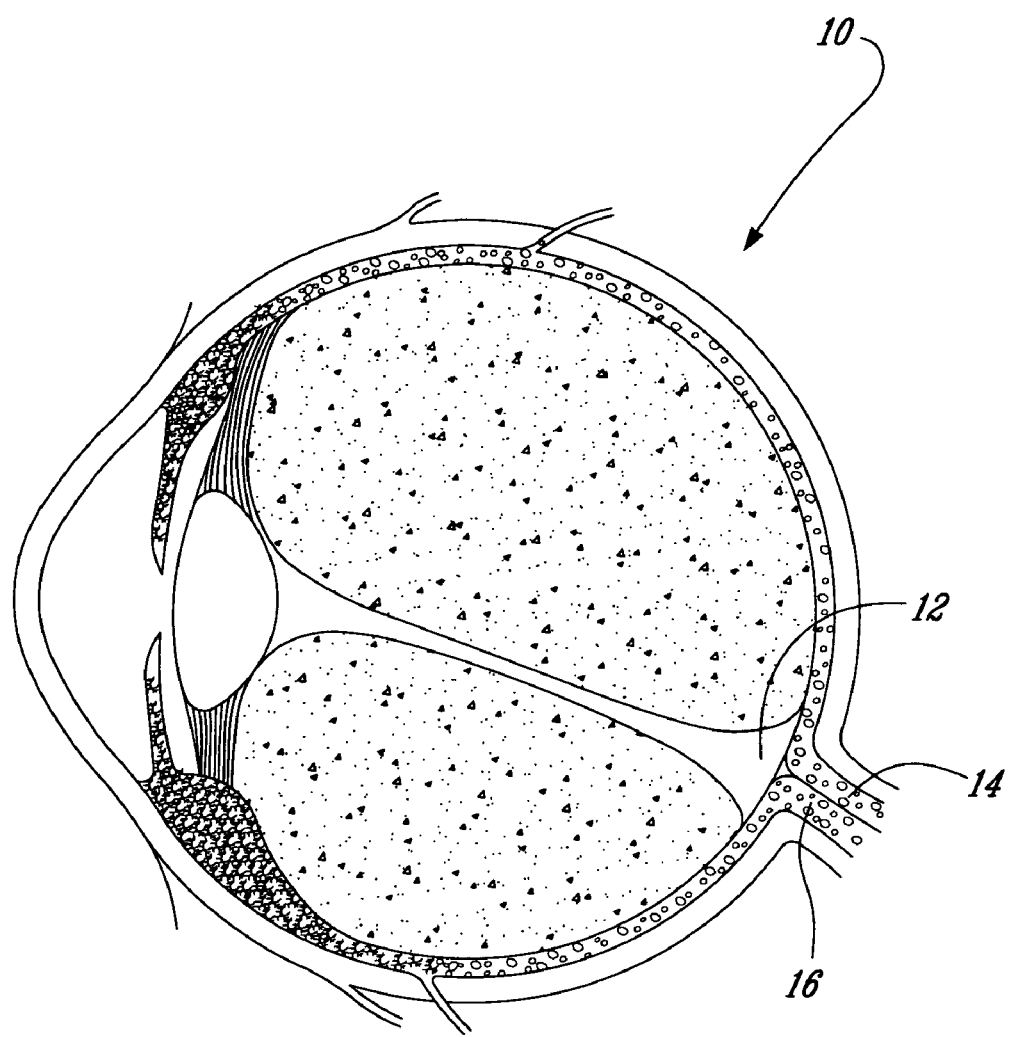
FIG. 1 shows a cross-sectional anatomical view of a human eye.

Reference is now made to FIG. 1, which depicts a cross-sectional view of an eye 10. The eye 10 includes a lamina cribrosa 12, which is a porous disc of specialized sclera through which axons 14 composing an optic nerve 16 leave the eye, and through which many capillaries and blood vessels feeding the optic nerve head and inner retina enter the eye 10. Axons 14 of the ganglion cells in the neuroretina form the retinal nerve fiber layer, and converge to form the optic nerve 16 head. These axons 14 then exit the eye 10 by passing through a specialized disc of sclera known as the lamina cribrosa 12. The lamina cribrosa 12 is a collagenous structure which is more porous than the sclera, in order to permit the exit of axons 14 and the entry of a vascular network that nourishes the optic nerve head (ONH) and retina.

Throughout the present specification, the terms biomechanical properties and displacement are being used alternatively. Displacement is one of the various biomechanical properties measured and/or assessed in the context of the present invention. The expression displacement is used herein generally as meaning an absolute movement of a movement relative to a reference point in the eye, where the reference point could be physiological, anatomical, optical or mechanical. Biomechanical properties include, without limitation, rigidity, elasticity, compliance, displacement, etc.

Known Facts about Glaucoma

Glaucoma is one of the various families of pathologies of the eye. As glaucoma progresses, the lamina cribrosa 12 becomes more exposed at the base of the cup of the optic disc becomes more exposed. It also bows backward, enlarges the size of its pores and, late in the course of glaucoma, becomes less compliant (more mechanically rigid). In fact, because of the requirement that it permits the exit of one million axons and allows the entry of countless elements of microvasculature while simultaneously acting as a pressure barrier between the intraocular and extraocular tissues, the lamina cribrosa has often been viewed as an anatomically vulnerable site in the pathophysiology of glaucoma. The fact that the pathognomonic finding of glaucoma, cupping, occurs in the optic nerve head reinforces the notion that the lamina cribrosa is a central actor in glaucoma.

Altered lamina cribrosa compliance has long been postulated to play a role in the development of open angle glaucoma. Lamina cribrosa mobility has been studied in ex vivo human and monkey eyes, in living human and monkey eyes and in histological studies. Some of these studies suggest that there may be an initial hyper compliance in early glaucoma, and most studies document a reduced compliance (i.e. increased rigidity) late in the course of the disease. Most investigators have hypothesized that reduced compliance contributes to the development of glaucoma (although there was no direct evidence for this), but no study has shown a link between reduced compliance and risk of progression. The hypothesized link between reduced laminar compliance and progression may be mistaken. Although the literature regarding lamina cribrosa compliance in glaucoma extends back one-quarter century, only in recent years has it become possible to measure some aspects of this compliance clinically.

Lamina cribrosa compliance can be estimated using confocal scanning laser opthalmoscopy (CSLO, [the specific commercial version in use is known as the Heidelberg Retina Tomograph]) by examining the position of the base of the cup relative to the retinal surface following long-term intraocular pressure (IOP) changes. The key parameter, which reflects lamina cribrosa position in almost all glaucoma patients, is the mean cup depth as measured by CSLO.

Potential Effect of Ocular Pulsatility

In the context of the present invention, some research was performed to explain the physiology of the eye and the lamina cribrosa, and more particularly the possible impact of ocular pulsatility.

Movement of the lamina cribrosa 12 occurs on different time scales. The movements involve long-term displacements of the lamina cribrosa 12 over weeks or months due to long-term variations in intraocular pressure. The same type of displacements likely occurs during the course of every 24-hour period due to diurnal variations in intraocular pressure. However there are also pulsatile changes in intraocular volume and intraocular pressure that occur with every cardiac cycle. These pulsatile changes in pressure impinging on the lamina cribrosa 12, neuroretinal rim and peripapillary tissues are potentially driven by vascular pulsations of the optic nerve head, choroid and retina. While the changes in pressures are relatively small, their anatomical sources suggest that they may cause stretching of the axonal fibers 14 in the optic nerve head. Since the vascular pulsations repeat with every cardiac cycle, their cumulative effect over months and years may be very significant. It is therefore important to measure the pulsatile blood flow of the optic nerve head and choroid, since it is this flow that drives the pulsatile displacements of the lamina cribrosa 12 during the cardiac cycle. The notion of mechanical changes in the optic nerve head being driven by the vasculature unites the mechanical and vascular theories of glaucoma.

The research performed in the context of the present invention demonstrates that this pulsatility is driven by an increased volume of blood in the choroid in systole. The choroid has the largest blood flow per gram of tissue of any organ in the human body. This choroidal pulsatility results in a pulsatile displacement of the cornea, as witnessed during applanation tonometry or Pulsatile Ocular Blood Flow (POBF), but also at the surface of the retina. The source of this ocular pulsatility is the choroid, which is sandwiched between the retina and the sclera. During systole, the retina moves anteriorly since it is in front of the expanding choroid. The wall of the eye expands during systole, as witnessed with the forward displacements of the cornea. The sclera and the lamina cribrosa must also move out from the center of the eye (the eye expands) slightly during systole. Therefore the axons of the nerve fiber layer (NFL), which begins on the vitreal surface of the retina and passes through the lamina cribrosa, must move anteriorly at the retinal surface during systole but posteriorly at the lamina cribrosa at the same time. These opposing movements could create stretch of nerve fibers potentially resulting in damage. It is the retinal nerve fiber layer that is the first observable damaged structure in glaucoma. It is evident that the lamina cribrosa movements that occur with ocular pulsations are smaller than those found with large long-term changes of IOP. Unlike long-term IOP changes that move the NFL (on the retinal surface) and the lamina cribrosa in the same direction (while moving the lamina more than the retinal surface), these smaller movements are believed more damaging to axons because of the stretching they cause. They are also more damaging because they occur 86,000 times per day.

The choroidal pulse amplitude varies between individuals. The evidence presented above demonstrates that the excursion of the lamina cribrosa during the cardiac cycle contributes to the risk of glaucoma damage. This excursion is determined by two primary factors: the biomechanical properties of the lamina cribrosa and the vascular pulsatility of the eye that drives the movements of the lamina. To estimate the biomechanical properties of the lamina cribrosa, it is preferable to control for the ocular pulsatility. The measurement of ocular pulsatility is accomplished by measuring the change in position of the macula with respect to the cornea during the cardiac cycle. More precisely, the method proceeds by centering on the macula for several heartbeats. The ratio between choroidal pulsatility and lamina cribrosa pulsatility is used to estimate the biomechanical properties of the lamina cribrosa.

Thus the measurement of the pulsatile biomechanical displacement of the lamina cribrosa is a key element in the assessment of an eye condition such as for example glaucoma. Based on the literature and the natural history of open angle glaucoma, the pulsatile movements of the lamina cribrosa increase (increased compliance) in the earliest stages of glaucoma compared to normal. As glaucoma progresses through the early stages, the pulse amplitude either remains high (in high risk patients) or begins to become smaller (protective decrease in compliance in glaucoma and ocular hypertensive patients having a lower risk of further visual field deterioration).

Apparatus

Based on those findings, an apparatus permitting identification of individuals with a high risk of rapid glaucoma progression, before further loss of vision occurs has been designed. The apparatus is adapted to measure displacement in proximity of the optic disc, and more particularly of the lamina cribrosa, synchronous with the cardiac cycle and use this data to estimate the lamina cribrosa's biomechanical properties. For doing so, the apparatus is adapted to measure the axial position of the lamina cribrosa in a living human eye with a spatial resolution of 1 µm and a temporal resolution of 10 msec.

In a particular aspect, the apparatus relies on optical interferometry to detect the pulsatile displacement of the lamina cribrosa synchronous with the cardiac cycle. A heterodyne interferometer for high spatial and temporal resolution measurements is also being used in an embodiment of the apparatus.

In another embodiment of the apparatus, pulsatile motion of the lamina cribrosa and its surrounding tissue, with a spatial resolution of 1 µm and a temporal resolution of 10 msec are being assessed. This embodiment of the apparatus allows measurements of multiple positions in and around the lamina cribrosa to obtain a complete understanding of its pulsatility and its relation to glaucoma.

Clinical Study

It has been proven in the context of the present invention that the position of the lamina cribrosa moves anteriorly to a variable degree when the IOP is reduced over the a long term period in glaucoma patients. If two eyes undergo the same change of IOP, the eye having the greater reduction of mean cup depth has a more compliant (less rigid) lamina. Modeling of CSLO data from patients shows that virtually all ONH pressure-dependant morphological changes, including those of the neuroretinal rim, are due to displacements of the underlying lamina. Thus, even in the minority of patients where the lamina is not well exposed, virtually all topographical disc changes are to some respect due to laminar displacements. Thus, even though a measure of lamina cribrosa compliance now exists, it is however cumbersome, requiring a change in Iop over a several week period, something that is not feasible for many patients. This technique, using the CSLO, also lacks both the temporal and the spatial resolution to detect and measure smaller short-term movements of the lamina cribrosa that occur with the cardiac cycle.

The pressure-dependant ONH topographical changes observed in the clinical study suggests that changes to laminar compliance occur early in the disease. There exist no prospective in vivo in situ studies on changes in lamina cribrosa compliance with the development of glaucoma in humans but the clinical study, discussed below, demonstrates that increased lamina cribrosa compliance (low rigidity) is associated with the rapid deterioration of visual fields in glaucoma patients.

Thus the clinical study examined the relationship between lamina cribrosa compliance and visual field progression. Twenty six patients underwent initial IOP reduction at which time their long-term lamina cribrosa compliance was assessed with CSLO. The patients were then followed for a mean 4.2 years. Patients that progressed had a mean 89+/−144 µm anterior displacement of the lamina cribrosa at the outset of the study, while in stable patients the corresponding value was 1+/−50 µm (p=0.039). Patients who progressed tended to have more compliant laminas. This finding implies that the development of increased laminar rigidity may actually be a protective adaptation which serves to limit subsequent damage from IOP fluctuations. In other words, eyes not adequately developing this adaptation may actually be at increased risk.

Substantial evidence points to defective ocular blood flow (OBF) in the pathogenesis of glaucoma. There is a delicate microvasculature that passes through the lamina cribrosa and nourishes the ONH. In the lamina, these capillary branches are organized predominantly in planes parallel to the wall of the eye and are therefore susceptible to compression and shearing by pressure-related displacements and compression of the lamina cribrosa. In eyes with more compliant laminas, the larger laminar displacement upon KW reduction may compress the microvasculature as it passes between the lamina cribrosa plates. Thus smaller improvements in neuroretinal rim blood flow were seen in patients with thinner corneas (and a more mobile lamina) compared to those with thicker corneas (35+/−80 units vs. 110+/−111 units, p=0.037), suggesting that the biomechanical properties of the lamina cribrosa has an important impact on ONH perfusion. Given the importance of blood flow in glaucoma, and the intimate anatomical relationship between the lamina cribrosa and the ONH vasculature, biomechanical changes of the lamina cribrosa contributes to vascular compromise to the ONH.

In a recent study made in the context of the present invention, the relationship between lamina cribrosa compliance and risk of deterioration in 32 patients with glaucoma or ocular hypertension was examined. In that study, following a sustained therapeutic 35% IOP reduction, the OSLO parameter mean cup depth shallowed by a mean value of 34+/−32 µm in the high-risk group but only by 4+/−36 µm in the low risk group (p=0.003). Patients were defined as high risk if they had thinner corneas, a parameter that has emerged from several large clinical trials as a major risk factor for progression of glaucoma. Maximum cup depth shallowed by 73+/−107 µm in the high-risk group but only 4+/−89 µm in the low risk (p=0.02). The suggestion from this study is that patients with greater risk of visual field deterioration have more compliant lamina cribrosas.

Three basic mechanisms thus underlie the association between thin cornea and greater lamina cribrosa movement:

A) a thin cornea is a marker for a thinner and therefore more mobile lamina cribrosa;

B) a thin cornea is a marker for a lamina cribrosa that has lower biomechanical rigidity, independent of its thickness. Altered connective tissue structure/biomechanical properties may be at fault here;

C) according to Laplace's Law, a thinner eye wall results in a greater stress on that wall for a given pressure.

Laplace's Law states that $$\text{Wall Stress} = \frac{\text{Pressure} \times \text{radius}}{\text{Wall thickness}}$$

Consequently, when a thinner wall (cornea, sclera, or lamina cribrosa) is present, there is greater stress on the lamina cribrosa and greater movement of the lamina when the pressure changes. Laplace's law has been used successfully by vascular physiologists to understand and predict the behavior of blood vessels and aneurysms. In many ways, the pressure-dependant backwards bowing of the lamina cribrosa in glaucoma resembles the development of an aneurysm.

Apparatus and Methods

The present invention thus provides a method and an apparatus with sufficient time resolution to measure the mechanical pulsatility of the optic nerve head or the lamina cribrosa. The method and apparatus of the present invention helps to 1) screen for glaucoma, 2) identify high risk glaucoma patients, 3) measure the biomechanical properties of the optic nerve head and 4) use molecular biological techniques to identify genes (and consequently, new therapies) associated with the phenotype of abnormal optic nerve head biomechanics and high-risk glaucoma.

The optic nerve head is influenced by many forces such as pulsatile intraocular pressure, vascular pulse amplitude, and scleral expansion forces and probably influenced by cerebrospinal fluid dynamics.

Therefore, a small amount of anterior-posterior displacements occurring at the lamina cribrosa 12, damages the axonal fibers 14 going through to the optic nerve 14. This process of axonal fiber 14 loss is unfortunately today only detectable at later stages of the glaucomatous disease.

As glaucoma is a disease affecting 2% of the population in North America, disease monitoring classically consider visual field loss, optic nerve cup enlargement and neuroretinal fibers loss to establish a prospective treatment according to the damaged parameters. However, these methods of detection have proven insufficient for detecting early stages of open angle and other forms of glaucoma, and to allow identification of patients at high risks of developing complications, especially visual losses.

The present invention allows in vivo in situ measurement of displacement in proximity of an optic disc, and in a particular embodiment of the lamina cribrosa. Some aspects of the method of the present invention further provide the possibility of assessing a condition of an eye, of screening for eye condition such as for example glaucoma, and of assisting in diagnosing people with high risk of developing certain eye condition such as glaucoma or allowing for establishing eye condition prognosis such as glaucoma evolution.

Displacements of the lamina cribrosa 12 in response to vascular pulsations are in the order of a few microns. It should be noted that although the following description refers to the measurement of the displacement of the lamina cribrosa, the apparatus and method of the present invention are not limited to the measurement of only that displacement. Because of its extreme accuracy and quasi real time measurements, the apparatus and method of the present invention is used to measure various biomechanical properties of the eye, which cannot be measured today because of the lack of proper apparatuses, and which the present invention addresses. Of particular note, the apparatus is well suited to measuring the pulsatile displacements of the retinal surface, which in turn are driven by the pulsatile blood flow of the underlying choroid. The apparatus is also well suited to measuring the pulsatile displacements of the cornea and therefore of estimating the biomechanical properties of the cornea. Therefore, throughout the following description, it should be clear that the use of the displacement of the lamina cribrosa should be understood as an example only, and not meaning to exclude other similar displacements of other parts of the eye.

Figure 2:
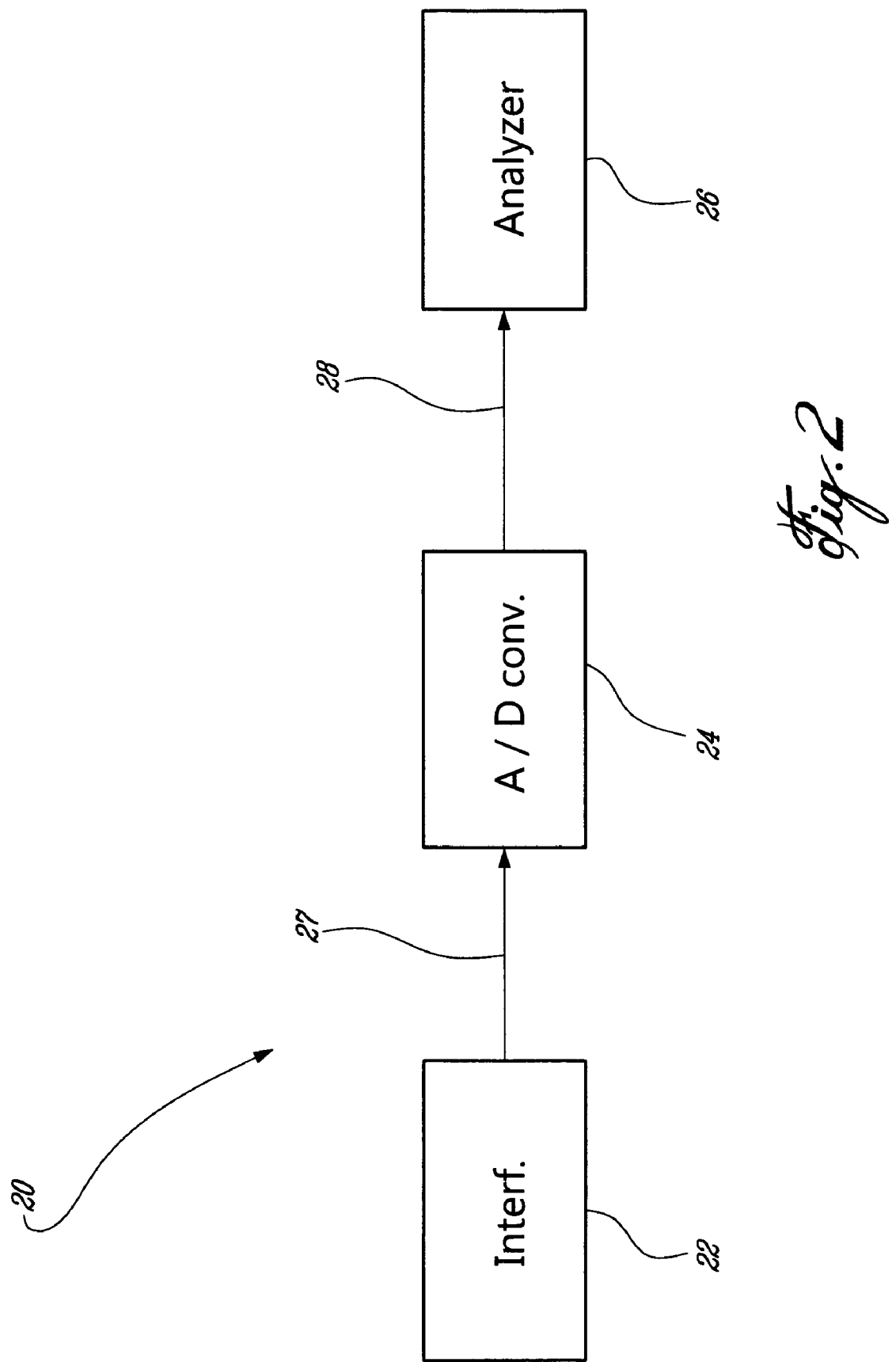
FIG. 2 is a schematic view of subcomponents of an apparatus in accordance with an aspect of the present invention.

Reference is now made to FIG. 2, which represents an apparatus 20 in accordance with a first aspect of the present invention. The apparatus 20 is composed of a probing unit, herein embodied by an interferometer 22, an analog/digital converter 24 and an analyzer 26. Other types of probing unit can alternatively be used without departing from the scope of the present invention. The probing unit is designed in such a manner that it allows safe and reliable probing of an eye in vivo in situ (not shown) and capable of detecting very small displacements therein. In a preferable manner, the probing unit is accurate enough that it allows detection of displacement of the lamina cribrosa, such as pulsatile displacement. The probing unit thus generates a resulting probing signal 27 corresponding to the displacement of the lamina cribrosa. The resulting probing signal 27 is received by the analog/digital converter 24, which converts the resulting probing signal 27 into a digitalized resulting probing signal 28, in accordance with techniques known in the field of digitalization of analog signals. For example, the analog/digital converter 24 could be an analog/digital converter from National Instruments'™, model AT-MIO-64E-3.

The analyzer 26 receives the digitalized resulting probing signal 28, and calculates and measures there from the displacement of the lamina cribrosa of the probed eye in vivo in situ. For example, the analyzer 26 may be a computer using dedicated software or a conventional spreadsheet software such as Excel™

Figure 3:
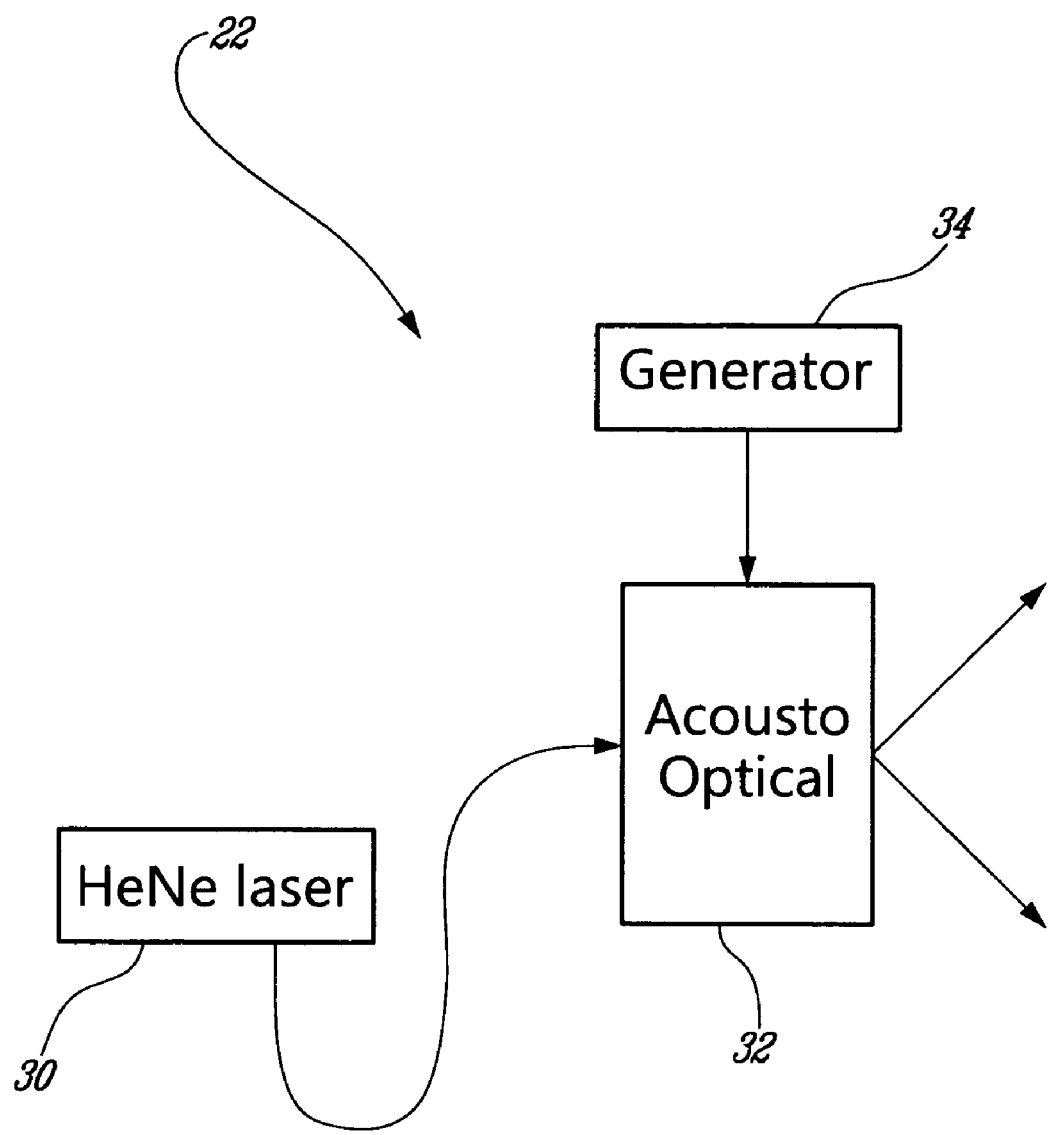
FIG. 3 is a schematic view of a portion of an interferometer of the apparatus in accordance with an embodiment of the present invention.

Reference is now made concurrently to FIGS. 2 and 3, wherein FIG. 3 is a schematic view of a portion of an interferometer 22 in accordance with an aspect of the present invention. To allow measurements in the range of microns, while respecting safety norms with respect to light intensity to probe the eye 10, it is important to improve the accuracy of the interferometer 22, without increasing the amplitude of a light beam used. For doing so, an aspect of the present invention relates to the defining, in operation, of at least two light paths of different frequencies by the interferometer 22. The interferometer 22 could for example consist of a Michelson interferometer. The building blocks of such an interferometer 22 include a monochromatic source 30, a detector (not shown), two mirrors (not shown) and one beam splitter (not shown). Typically, in such an interferometer, a light beam is generated by the monochromatic source 30, which could for example be a HeNe laser. Considering the light absorption by eye tissue, the monochromatic source 30 could also be for example a frequency-stabilized laser in the near-infrared.

Michelson interferometers and interferometers in general are widely known in the field of interferometry, and thus are not explained in greater detail in the present application. However, in the context of the present invention, an improvement is added to the interferometer 22 so as to increase its accuracy. The light beam of the monochromatic source 30 is first modified by an acoustic-optical cell 32, prior to entering the beam splitter. The acoustic-optic cell 32 is composed of piezoelectric crystals which, under electro-acoustic fields, can modify the light beam to produce two light beams of different frequencies 36. The difference in frequencies between the two light beams may be varied from very small differences, i.e. a couple of Hz, to larger differences, i.e. kHz or MHz, depending on the accuracy required. More particularly, in accordance with one aspect of the present invention, a combination of two different, but close, frequencies for the two light paths produce a probing resulting signal 27 having a difference in phase that is proportional to the displacement of the probed lamina cribrosa. It should be noted that other methods of achieving different frequencies of two light paths generated by a monochromatic source 30 could be used, without departing from the scope of the present invention.

For example, in the context of the present invention, a commercially available interferometer has been used to perform testing, so as to determine the required accuracy. The interferometer that was used to perform such testing was the Precision Optic Displacement Sensor (PODS), manufactured and sold by MPB Communications Inc. The PODS is based on Michelson's interferometer, and avoids one of the problems generated in regular interferometry measurements that arises from the fact that both laser beam paths with different intensity may generate a false interpretation of displacement. It was however noted that the PODs, despite its intrinsic versatility, high spatial resolution and exceptional bandwidth, still needed some additional fine-tuning so as to obtain an accurate measurement of the displacement of the lamina cribrosa, and more particularly for the measurement of its pulsatile displacement. For example, a standard avalanche photodiode detector with 7 MHz temporal response was replaced by other types of light detectors having higher detection sensitivity. The other types of light detectors (a) a different avalanche photodiode with lower temporal response but higher sensitivity, (b) photomultiplier tubes or (c) hybrid photodetectors which are basically photomultiplier tubes with avalanche photodiodes. In order to get even higher sensitivity, it was also noted that it is possible to use the lock-in amplification technique. This technique uses a signal synchronized with the light beam to efficiently increase the signal-to-noise ratio of the measurement.

For doing so, an aspect of the present invention further provides for improving the sensitivity of the interferometer 22 by heterodyning the at least two light paths defined by the present interferometer 22. Such heterodyning of the at least two light paths allows probing of displacements of the lamina cribrosa in the order of nanometers. In an heterodyned interferometer, a second laser beam is generated by transmitting the first laser beam through an acousto-optic modulator. The second laser beam has a slightly different wavelength compared with the first laser beam. Heterodyning is performed by using the first laser beam and the second laser beam within the interferometer.

Figure 4:
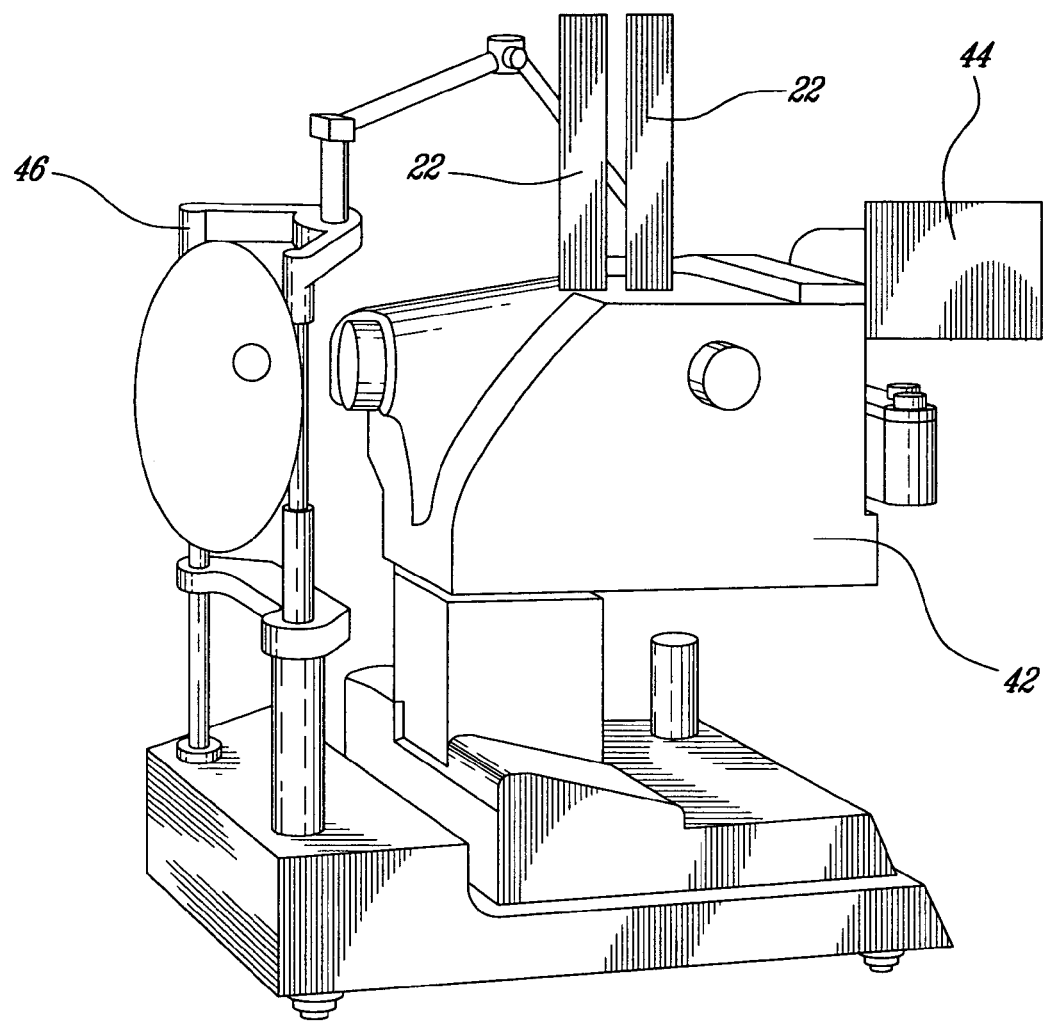
FIG. 4 is a perspective view of an apparatus in accordance with an embodiment of the present invention.

Turning now to FIG. 4, there is depicted a perspective view of a portion of an apparatus in accordance with another aspect of the present invention. The portion of the apparatus depicted in FIG. 4 is an exemplary representation of the physical components of the apparatus 10 that would be used by an ophthalmologist, optometrist or any other vision specialist, to perform measurement of the displacement of the lamina cribrosa, in accordance with the present invention. FIG. 4 does not depict components such as the analog/digital converter 24 and the analyzer 26 for reasons of clarity. FIG. 4 thus depicts a fundus camera 42, a camera 44, and a probing unit composed of two interferometers 22 for exemplary purposes. The fundus camera 42 is a camera often used by eye specialists to observe the back of the eye. The fundus camera 42 preferably comes with a headrest 46, where a patient places his/her head for immobilization, and providing stability for performing the probing and measuring of the present invention. The camera 44 may be for example a Pulnix 200 NIR™, which allows visualizing the optic nerve 16 and lamina cribrosa 12 with a subtended 30 degrees visualization angle providing 10× magnification.

In use, a patient is seated in a chair. The patient's head is supported in the head support 46 such that his/her head is restricted from moving as much as possible. The fundus camera 42 is placed towards the patient's eye such that the interferometers 22 are directed in a pupil. The fundus camera 42 is used to visualize the optic nerve head during measurements and examination. The fundus camera 42 is also used for properly positioning the laser beam of the interferometers 22 onto the position of measurement. The vibration of the lamina cribrosa 12 is measured by first probing the lamina cribrosa 102 itself using one of the interferometers 22, and then using the other interferometer 22 and pointing at tissues surrounding the lamina cribrosa 12. For example, it could be desired to point at tissues surrounding the lamina cribrosa 12, which move in the opposite direction of the lamina cribrosa during cardiac pulsations. This way, it is possible to subtract external vibrations (such as the movement of the patient, cardiac pulsation etc.), using the two interferometers 22. Therefore, the pulsatile component of the anterior-posterior displacement of the lamina cribrosa 12 can be isolated. Once properly positioned, both interferometers 22 start their probing and generate two corresponding resulting probing signals. The resulting probing signals are treated as previously described in reference of FIG. 2. Finally, the relative displacement of the two positions as a function of time is calculated and displayed.

Clinical Results

The apparatus of the present invention has been used to perform tests on ex vivo eyes and eyes in vivo in situ. For ex vivo measurements, the motion of a dissected lamina cribrosa tissue mounted onto a vibrating stage was measured. A lens was used to focus the monochromatic source of the precision optic displacement sensor onto the tissue, which focal length was 25 mm, to model the focusing capability of a human eye. The results proved that the precision optic displacement sensor is capable of such measurement. However, it also revealed that the detection was close to its threshold, due mainly to the low power level of the laser scattered from the lamina cribrosa. As a result, the alignment of the tissue, lens and laser was highly critical for the correct measurement of displacement. This work clarified what improvements were required to the currently available PODS for applying this technique to measurement of biomechanical properties of live eyes. In vivo in situ measurements of the motion of the cornea surface of an anesthetized pig were performed. The pig was laid onto a normal surgical table without any fixation. A lens was used to focus the monochromatic source of precision optic displacement sensor onto the cornea surface, and to collect and collimate the scattered laser for measurement. The pulsatility of the pig cornea was successfully measured with a maximum displacement of 30 µm synchronous with the cardiac cycle.

Figure 5:
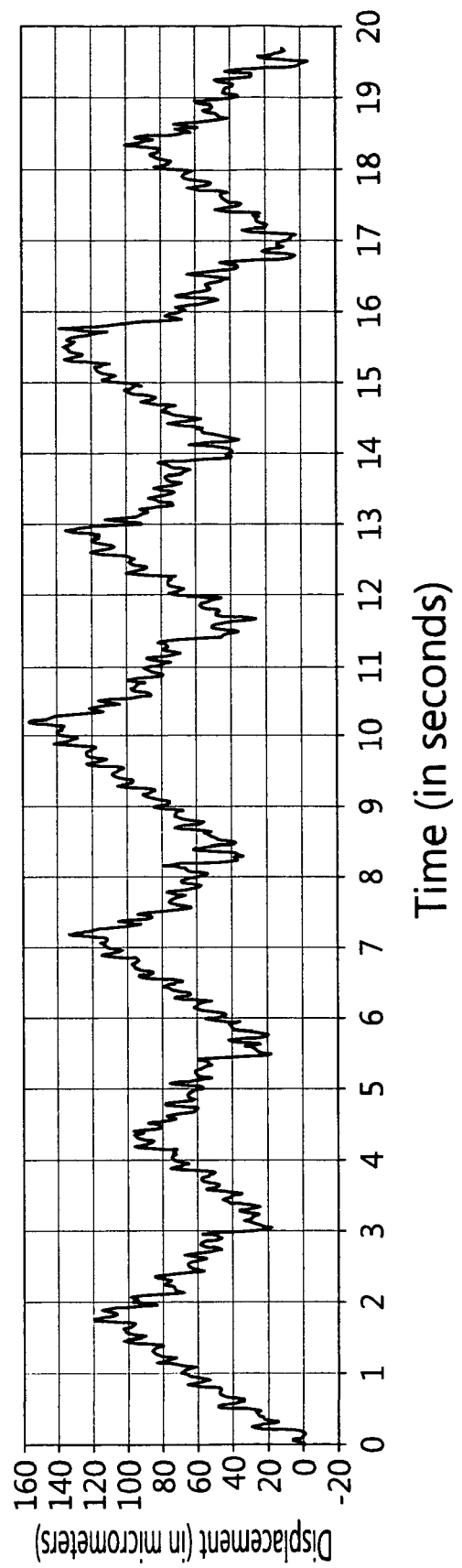
FIG. 5 is a graph representing measurements of corneal displacement over time.
Figure 6:
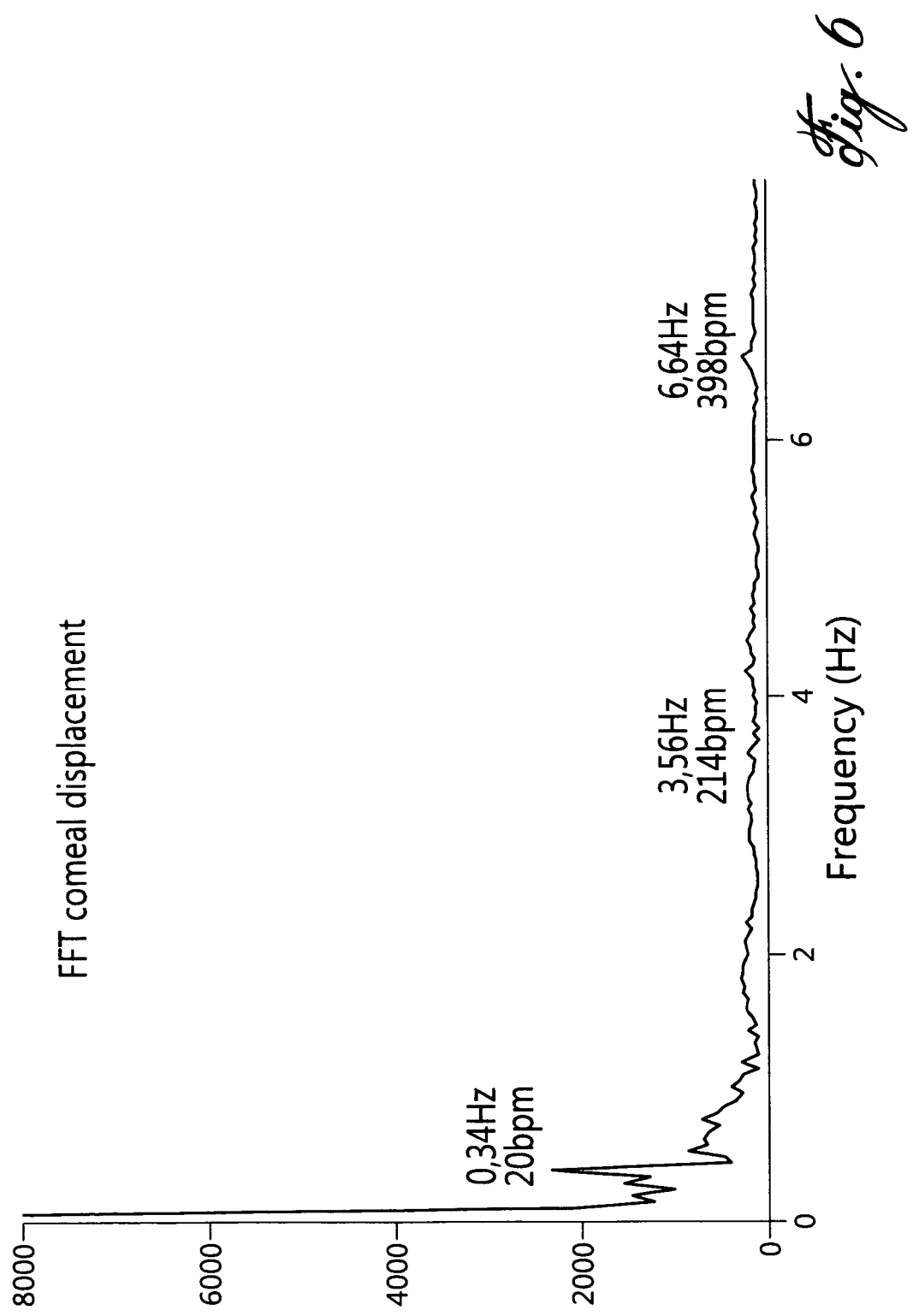
FIG. 6 is a graph representing measurements of corneal displacement in a frequency domain.
Figure 7:
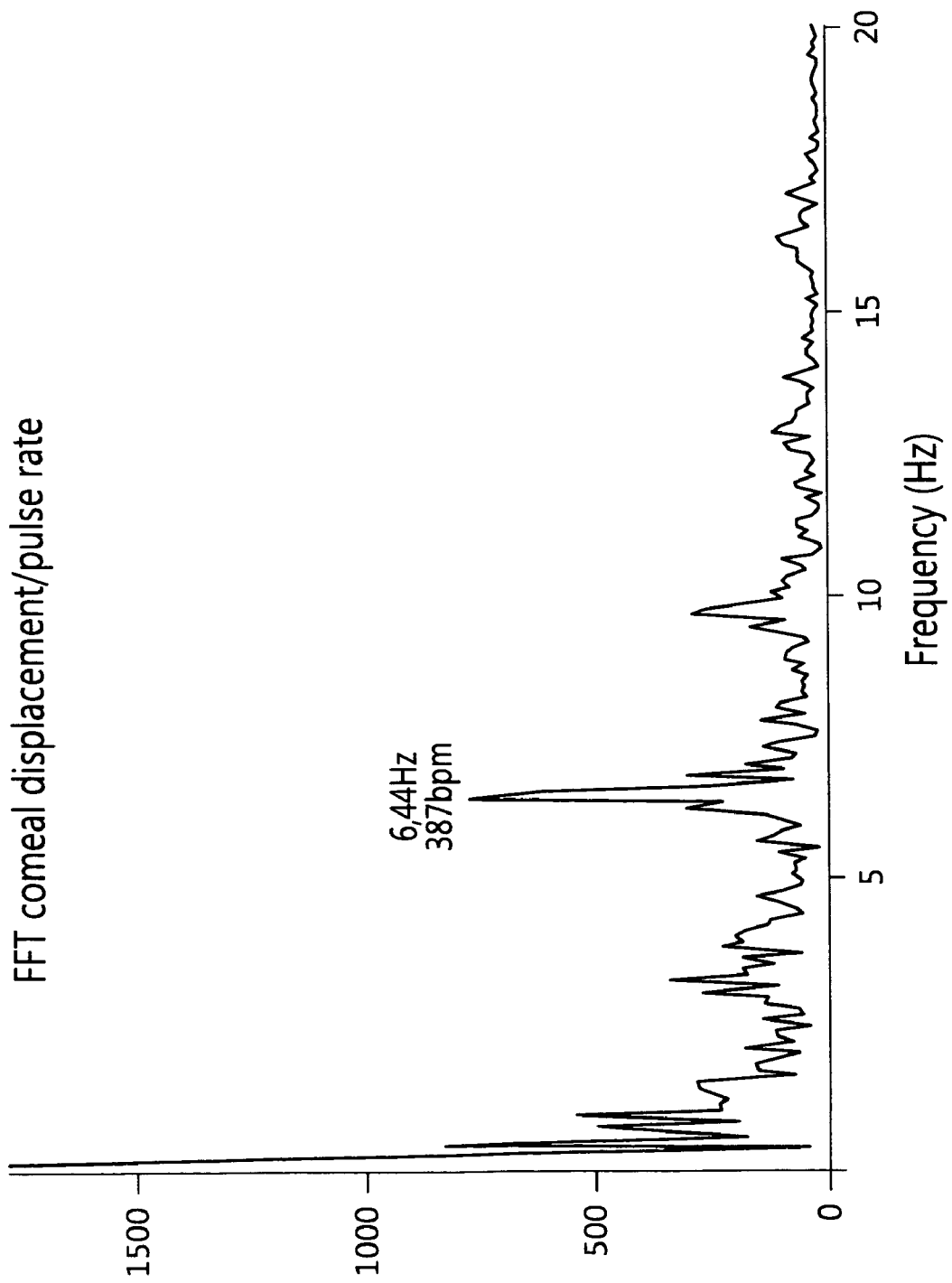
FIG. 7 is a graph representing measurements of corneal displacement with pulse rate in a frequency domain.

In another aspect, corneal and fundus mechanical displacements were measured by interferometry on a New Zealand rabbit. The rabbit was anesthetised with intramuscular injection of Ketamine 50 mg/kg and Acepromazine 1 mg/kg subcutaneous. This method allows approximately between 1½ and 2 hours of anaesthesia. Then, the animal was placed on a dedicated positioning table with head tilt capabilities to allow the incidence of the probing laser beam in a perpendicular fashion to the corneal apex. The head was fixed to the headrest and dilated with tropicamide 1%. An ophthalmic speculum was used for this purpose. After warming up the HeNe laser for 20 minutes for stability, the probing beam was focused into the fundus while observing the image over two monitors: one for the fundus imaging and the second one to align the fundus reflection precisely onto the avalanche photodiode detector. This method was accomplished by moving the aspheric lens in the three possible dimensions (X, Y and Z) in front of the device. Once both images were clear, especially dedicated software was run to control the demodulator and the acquisition board as well. The signal was then digitally recorded in the computer's hard drive. By steering the beam polarization with the optical system, it was possible to acquire or reject the reflected beam coming from the cornea. Therefore, corneal and fundus displacements were recorded and compared. FIGS. 5, 6 and 7 are graphs representing measurements obtained during this experiment. More particularly, FIG. 5 is a graph depicting the measurements made of corneal displacement over time, FIG. 6 is a graph representing measurements of corneal displacement in a frequency domain, and FIG. 7 is a graph representing measurements of corneal displacement with pulse rate in a frequency domain.

By being able to accurately measure biomechanical properties of an eye in accordance with the present invention, it is thus possible to evaluate and potentially diagnose an eye of a patient, for diseases such as glaucoma. More particularly, by determining in vivo in situ biomechanical properties of the lamina cribrosa, it is possible to correlate the biomechanical properties with an eye disease. The biomechanical properties may include for example displacement of the lamina cribrosa, or a pulsatile displacement thereof. For determining the in vivo in situ biomechanical properties, the present apparatus, or any other apparatus capable of safely measuring displacement in the order of nanometers in the eye in vivo in situ, could be used to measure the pulsatile displacement of the lamina cribrosa, to measure an anterior-posterior displacement of a point on a retina next to the lamina cribrosa, and to compare the measured pulsatile displacement of the lamina cribrosa and the measured anterior-posterior displacement of the peripapillary retina. In a preferable manner, the measuring is performed by probing an eye region encompassing the lamina cribrosa and by probing the anterior-posterior displacement of the peripapillary retina in at least three different points. In another embodiment of the present invention, the measuring of the anterior-posterior displacement of the peripapillary retina and the measuring of the pulsatile displacement of the lamina cribrosa are performed simultaneously. For efficiency purposes, the present invention also allows for performing the probing and measuring in real time. It should be clear that the apparatus of the present invention could be used to measure a biomechanical property of an eye in vivo in situ, such as for the measurement of anterior-posterior pulsatile displacement of the lamina cribrosa.

The present invention has been described with regard to preferred embodiments. The description as much as the drawings are intended to help the understanding of the invention, and do not limit its scope. It will be apparent to one skilled in the art that various modifications may be made to the invention without departing from the scope of the invention as described herein.

The invention claimed is:

1. An apparatus for measuring displacement in an eye in vivo in situ, the apparatus comprising:
    a probing unit for probing in vivo in situ an eye for displacement of at least two distinct points in proximity of an optic disc, the probing unit generating a corresponding resulting probing signal;
    an analog/digital converter for converting the resulting probing signal into a digitalized resulting probing signal; and
    an analyzer for analyzing the digitalized resulting probing signal and assessing therefrom displacement in proximity of the optic disc of the eye.

2. The apparatus of claim 1, wherein the probing unit is an interferometer defining two light paths of different frequencies, for probing the eye at least at two distinct points in proximity of the optic disc.

3. The apparatus of claim 2, wherein the two distinct points are a lamina cribrosa and a peripapillary retina.

4. The apparatus of claim 3, wherein the probing unit particularly probes a pulsatile displacement of the lamina cribrosa relative to the peripapillary retina.

5. The apparatus of claim 1, wherein the analyzer further determines whether the displacement of at least two distinct points is within a normal range.

6. A method of assessing condition of an eye in a patient comprising:
    measuring in vivo in situ a displacement of at least two distinct points in proximity of an optic disc of the eye; and
    correlating the measured displacement with an eye condition.

7. The method of claim 6, wherein the measuring is performed at least two distinct points consist of a lamina cribrosa and a peripapillary retina of the eye.

8. The method of claim 7, wherein the measuring of the peripapillary retina displacement and the measuring of the pulsatile displacement of the lamina cribrosa are performed simultaneously.

9. The method of claim 6, wherein the displacement is a pulsatile displacement.

10. The method of claim 9, wherein the correlating is effectuated by:
    comparing measured pulsatile displacement of the lamina cribrosa and measured peripapillary retina displacement.

11. The method of claim 6 wherein the eye condition is glaucoma.

12. A method for identifying an eye having an elevated risk of rapid visual field deterioration, the method comprising steps of:
    measuring in vivo in situ a displacement of at least two distinct points in proximity of an optic disc of the eye; and
    correlating the measured displacements with an eye condition.

13. The method of claim 12, wherein the measuring is performed in two distinct points consisting of a lamina cribrosa and a peripapillary retina of the eye.

14. The method of claim 13, wherein the correlating is effectuated by:
    comparing measured pulsatile displacement of the lamina cribrosa and measured peripapillary retina displacement.

15. The method of claim 13 wherein the measuring of the peripapillary retina displacement and the measuring of the pulsatile displacement of the lamina cribrosa are performed simultaneously.

16. The method of claim 12, wherein the displacement is a pulsatile displacement.

* * * * *